United States Patent
Roy et al.

(10) Patent No.: US 11,376,338 B2
(45) Date of Patent: *Jul. 5, 2022

(54) USE OF THERMOSTABLE RNA POLYMERASES TO PRODUCE RNAS HAVING REDUCED IMMUNOGENICITY

(71) Applicant: New England Biolabs, Inc., Ipswich, MA (US)

(72) Inventors: Bijoyita Roy, Medford, MA (US); G. B. Robb, Somerville, MA (US)

(73) Assignee: New England Biolabs, Inc., Ipswich, MA (US)

( * ) Notice: Subject to any disclaimer, the term of this patent is extended or adjusted under 35 U.S.C. 154(b) by 281 days.

This patent is subject to a terminal disclaimer.

(21) Appl. No.: 16/616,734

(22) PCT Filed: Jun. 12, 2018

(86) PCT No.: PCT/US2018/036996
§ 371 (c)(1),
(2) Date: Nov. 25, 2019

(87) PCT Pub. No.: WO2018/236617
PCT Pub. Date: Dec. 27, 2018

(65) Prior Publication Data
US 2021/0147836 A1   May 20, 2021

Related U.S. Application Data

(60) Provisional application No. 62/522,877, filed on Jun. 21, 2017.

(51) Int. Cl.
| | | |
|---|---|---|
| *A61K 48/00* | (2006.01) | |
| *C12P 19/34* | (2006.01) | |
| *A61K 31/713* | (2006.01) | |
| *C12N 9/12* | (2006.01) | |
| *A61K 31/7105* | (2006.01) | |
| *C12N 15/113* | (2010.01) | |

(52) U.S. Cl.
CPC ........ *A61K 48/0091* (2013.01); *A61K 31/713* (2013.01); *A61K 31/7105* (2013.01); *C12N 9/12* (2013.01); *C12N 9/1247* (2013.01); *C12N 15/113* (2013.01); *C12P 19/34* (2013.01); *C12Y 207/07006* (2013.01); *C12N 2310/122* (2013.01); *C12N 2310/141* (2013.01); *C12N 2310/17* (2013.01)

(58) Field of Classification Search
CPC ............ A61K 48/0091; A61K 31/7105; C12N 15/111; C12N 9/1247; C12N 15/1068
See application file for complete search history.

(56) References Cited

U.S. PATENT DOCUMENTS

| 6,524,828 B1* | 2/2003 | Liao ..................... C12N 9/1247 435/320.1 |
| 7,507,567 B2* | 3/2009 | Sugiyama ............ C12N 9/1247 435/183 |
| 8,383,340 B2 | 2/2013 | Ketterer et al. |
| 8,551,752 B2* | 10/2013 | Oe ....................... C12N 9/1247 435/194 |
| 9,193,959 B2* | 11/2015 | Sobek .................. C12N 9/1247 |
| 2013/0259923 A1* | 10/2013 | Bancel ............... A61K 48/0066 424/450 |
| 2016/0280748 A1 | 9/2016 | Liu et al. |
| 2017/0247410 A1 | 8/2017 | Weller et al. |
| 2017/0247670 A1* | 8/2017 | Ong ..................... C12N 9/1247 |

FOREIGN PATENT DOCUMENTS

| JP | 2003125767 A | 5/2003 |
| WO | 200166705 A1 | 9/2001 |
| WO | 2007/024708 A2 | 3/2007 |
| WO | 2010/043630 A2 | 4/2010 |
| WO | 2013102203 A1 | 7/2013 |
| WO | 2014/144711 A1 | 9/2014 |
| WO | 2014144767 A1 | 9/2014 |
| WO | 2016077294 A1 | 5/2016 |

OTHER PUBLICATIONS

Kim, J. Y. et al. :"Immune activation by siRNA/liposome complexes in mice is I-12 sequence-independent: lack of a role for Toll-like receptor 3 signaling.", Molecules and Cells, vol. 24, No. 2, 2007, pp. 247-254.
Devoldere, et al., (2016), Drug Discover Today, 21(1), 11-25.
Loomis, et al., (2016), Journal of Materials Chemistry 4:1619-32.
Triana-Alonso, et al., (1995), The Journal of Biological Chemistry, 270 (11): 6298-6307.
Kariko, et al., (2005) Immunity, 23:165-175.
Kariko, et al., (2011) Nucleic Acids Research, 39 (21), e142.
Weissman, et al., (2012) Methods in Molecular Biology, 969:43-54.
Koubek et al., (2013) RNA, 10:1449-59.
Vandebriel,et al Hum. Vaccin. Immunother. 2012 8: 1323-1325.
Joubert, et al PLOS One 2016, 11(8): e0159328.
Stickler, et al Toxicological Sciences 2004 77:280-289.
Kariko, et al., Nucleic Acids Research, 39, 21, e142, 2011.
Mellits, et al., Nucleic Acids Research, 18, 18, 5401-5406, 1990.

* cited by examiner

*Primary Examiner* — Dana H Shin
(74) *Attorney, Agent, or Firm* — New England Biolabs, Inc

(57) ABSTRACT

Provided herein, among other things, is a method for producing an RNA product that has reduced immunogenicity. In some embodiments, the method involves transcribing a template DNA with a thermostable RNA polymerase at a temperature of greater than 44° C.

11 Claims, 5 Drawing Sheets

Specification includes a Sequence Listing.

Wild-type T7_RNAP

Thermostable T7_RNAP

Wild-type T7_RNAP (55°C)

Thermostable T7_RNAP (55°C)

SEQUENCE LISTING

<160> NUMBER OF SEQ ID NOS: 1

<210> SEQ ID NO 1
<211> LENGTH: 883
<212> TYPE: PRT
<213> ORGANISM: Artificial Sequence
<220> FEATURE:
<223> OTHER INFORMATION: Synthetic construct

<400> SEQUENCE: 1

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

```
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
            690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
            755                 760                 765
Ile Asp Ala His Lys Gln Glu Ser Gly Ile Ala Pro Asn Phe Val His
            770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
            835                 840                 845
Phe Ala Asp Gln Leu His Glu Ser Gln Leu Asp Lys Met Pro Ala Leu
```

```
              850                 855                 860
Pro Ala Lys Gly Asn Leu Asn Leu Arg Asp Ile Leu Glu Ser Asp Phe
865                 870                 875                 880

Ala Phe Ala
```

USE OF THERMOSTABLE RNA POLYMERASES TO PRODUCE RNAS HAVING REDUCED IMMUNOGENICITY

CROSS REFERENCE

This application is a § 371 application of International Application No. PCT/US2018/036996, filed Jun. 12, 2018, which claims the benefit of U.S. Provisional Application No. 62/522,877, filed Jun. 21, 2017. The entire contents of these applications are incorporated herein by reference in their entirety.

BACKGROUND

Synthetic RNAs are a promising new class of therapeutics for non-virus-mediated gene therapy, vaccines and protein replacement therapeutics, as well as in immuno-oncology and personalized cancer vaccines (Sahin, et al., (2014): Nature Reviews Drug Discovery 13, 759-80; Weissman, (2015), Expert Review of Vaccines, 14(2):265-81). Synthetic RNAs are commonly manufactured by in vitro transcription (IVT) of a DNA template that encodes the antigen or protein of interest (Sahin, et al., (2014); Steinle, et al., (2017), Stem Cells, 35(1):68-79).

One limitation associated with the therapeutic use of synthetic RNA is an immunostimulatory response induced by double-stranded RNA (dsRNA) contaminants created during IVT (Devoldere, et al., (2016), Drug Discover Today, 21(1), 11-25; Loomis et al., (2016), Journal of Materials Chemistry 4:1619-32; Triana-Alonso et al., (1995), The Journal of Biological Chemistry, 270 (11): 6298-6307). The immunostimulatory response of cells results from activation of receptors that trigger secretion of interferons and inflammatory cytokines (Devoldere et al., (2016); Loomis et al., (2016); Kariko, et al., (2005) Immunity, 23:165-175).

Several methods have been developed to separate desired IVT products from contaminating dsRNA. These include various chromatography techniques such as: ion exchange high-performance liquid chromatography (HPLC), reverse phase HPLC, hydrophobic interaction HPLC, low or normal pressure liquid chromatography, size exclusion chromatography, oligo dT affinity chromatography, and core bead chromatography (Kariko, et al., (2011) Nucleic Acids Research, 39 (21), e142; Weissman, et al., (2012) Methods in Molecular Biology, 969:43-54; Kobuk, et al., (2013) RNA, 10:1449-59; US 2016/0024141; US 2016/0024140 A1; U.S. Pat. No. 8,383,340; WO 2014/144711; US 2016/0032316; US 2014/144767; US 2016/0326575). Enzymatic digestion of dsRNA with RNase III, RNase V1, Dicer, and Chipper is also implemented to reduce dsRNA (US 2016/0032316).

The use of a physical separation method to remove the dsRNA from IVT reactions increases the cost and labor involved in the production of IVT RNAs that minimally activate innate immune responses.

SUMMARY

It has been found that IVT of a DNA template at an elevated temperature (e.g., at a temperature of greater than 44° C.) produces an RNA product that is less immunostimulatory than RNA products that are produced at a lower temperature (at 37° C.). Without wishing to be bound to any specific theory, it is believed that RNA products produced at an elevated temperature are less immunostimulatory than those produced at a lower temperature because they contain less dsRNA, which is known to have an immunostimulatory effect. As such, in some embodiments, the RNA products produced at an elevated temperature can be transfected into cells without first removing the dsRNA from the RNA product, i.e., without first purifying the non-dsRNA products from the RNA product (such as using chromatography or degrading the dsRNA enzymatically).

A variety of methods and compositions are described herein. In some embodiments, the method may comprise: (a) transcribing a template DNA with a thermostable RNA polymerase at a temperature of greater than 44° C. to produce an RNA product; and (b) introducing (e.g. transfecting) the RNA product into mammalian cells. Because the RNA product produced by this method does not contain significant amounts of dsRNA (has a reduced dsRNA content as compared to a control RNA product produced from the same template using the same RNA polymerase but at a lower temperature of only 37° C.), the method may be done in the absence of a step that removes dsRNA from the RNA product prior to introducing the RNA product into the mammalian cells.

Embodiments provide a method comprising: (a) transcribing a template DNA with a thermostable RNA polymerase at a temperature of greater than 44° C. (such as at a temperature of at least 50° C.) to produce an RNA product; and (b) measuring the immunogenicity of the RNA product in the absence of a step that removes any dsRNA from the RNA product.

The thermostable RNA polymerase may be a variant of a bacteriophage RNA polymerase, such as a thermostable variant of the wild type T7 RNA polymerase having the amino acid sequence shown in SEQ ID NO:1.

The RNA product may be a protein, such as a therapeutic protein. The RNA product may be a therapeutic RNA and/or may be a guide RNA, a short hairpin RNA, a siRNA, a microRNA, a long noncoding RNA, an mRNA encoding a recombinant protein or a native protein, an RNA containing modified nucleotides, and a capped mRNA.

The immunogenicity of the RNA product may be measured by any known means. For example, the immunogenicity may be measured by assaying the RNA product for the presence of dsRNA. As discussed herein, dsRNA is known to have an immunostimulatory effect. The presence or amount of dsRNA can therefore be correlated with immunogenicity of the RNA product. Alternatively, or in addition, the immunogenicity of the RNA product may be measured by introducing the RNA product into one or more mammalian cells. The mammalian cells may be cells of a mammalian subject in vivo (i.e. the RNA product is administered to a mammal, such as a test mammal; and an immune response in the mammal is measured). Alternatively, or in addition, the mammalian cells may be mammalian cells cultured in vitro or mammalian cells ex vivo (in which case the RNA product is introduced into the cells, such as by transfection; and an immune response in the cells is measured, such as using an enzyme-linked immunosorbent assay (ELISA) to determine the level of e.g. IFN-α and/or TNF-α in the cell supernatant).

The method may involve comparing the immunogenicity measured for the RNA product with the immunogenicity measured for a control RNA product. The control RNA product may be produced by transcribing the template DNA with the thermostable RNA polymerase at a temperature of 37° C., in the absence of a step that removes any dsRNA from the control RNA. Thus, the method may further comprise: (i) producing a control RNA product by transcribing the template DNA with the thermostable RNA polymerase at a temperature of 37° C. and, in the absence of a step that removes any dsRNA from the control RNA product, measuring the immunogenicity of the control RNA product; and (ii) comparing the immunogenicity measured for the RNA product with the immunogenicity measured for the control RNA product. The immunogenicity of the control RNA product may be measured by any known means; such as by assaying the control RNA product for the presence of dsRNA, by introducing the control RNA product into cells of a mammalian subject in vivo, or by introducing the control RNA product into mammalian cells cultured in vitro or into mammalian cells ex vivo.

Embodiments also provide a method comprising: (a) transcribing a template DNA with a thermostable RNA polymerase at a temperature of greater than 44° C. to produce an RNA product; and optionally measuring the immunogenicity of the RNA product (e.g. using any technique described herein); and (b) combining the RNA product with a pharmaceutically acceptable excipient; wherein the method is done in the absence of a step that removes any dsRNA from the RNA product between steps (a) and (b).

BRIEF DESCRIPTION OF THE FIGURES

The skilled artisan will understand that the drawings, described below, are for illustration purposes only. The drawings are not intended to limit the scope of the present teachings in any way.

FIG. 1A shows the results from transcription with wild-type T7 RNA polymerase at 37° C.

FIG. 1B shows the results from transcription with a thermostable variant of T7 RNA polymerase at 37° C. At 37° C., both wild-type and the thermostable variant of RNA polymerase generated the desired RNA product (1.2% agarose gel) and contaminating dsRNA (immunoblot) regardless of the length of the DNA template.

FIG. 2A shows, using wild-type T7 RNA polymerase, dsRNA detected by mAb J2 (English and Scientific Consulting, Budapest, Hungary) in IVT reaction mixtures at temperatures between 37° C. and 55° C. The polymerase activity is lost at temperatures greater than 43.9° C., as determined by the absence of IVT Cluc NotI RNA. Moreover, dsRNA was detected in IVT reaction mixtures using the mAb J2 (English and Scientific Consulting, Budapest, Hungary) at temperatures between 37° C. and 43.9° C.

FIG. 2B shows, using a thermostable T7 polymerase, dsRNA detected by mAb J2 in IVT reaction mixtures at temperatures between 37° C. and 55° C. The detectable amount of dsRNA is substantially reduced at temperatures greater than 44° C. while the amount of IVT Cluc NotI RNA produced at the same time using thermostable T7 RNA polymerase is significant.

FIG. 2C shows, using wild-type T7 RNA polymerase, that both the amount of IVT RNA and dsRNA from DNA templates of different lengths are substantially reduced at temperatures of 55° C.

FIG. 2D shows, using a thermostable T7 RNA polymerase, that only dsRNA contaminants in IVT mix from DNA templates of different lengths are substantially reduced at temperatures of 55° C. while at the same time the yields of IVT were significant and similar throughout.

FIG. 5A shows the results of absolute quantification of IFN-α (interferon) levels in the cell culture supernatants of hDCs that were transfected with Cluc NotI IVT RNA using ELISA (Kariko, et al., (2011)). Cluc NotI IVT RNA (or control RNA—poly I:C) was introduced into hDCs, and supernatants were collected 24 hours after transfection. The supernatants were then probed for the secretion of IFN-α. Higher interferon secretion is observed with Cluc NotI IVT RNA from 37° C. transcription reactions without subsequent removal of the dsRNA (IVT 37° C.) as compared to Cluc NotI IVT RNA from 55° C. transcription reactions without subsequent removal of the dsRNA (IVT 55° C.) or HPLC-purified Cluc NotI IVT RNA (IVT 37° C._HPLC) indicating low immunostimulatory properties of IVT RNA synthesized at 55° C. Increased secretion of IFN-α is seen with polyI:C (positive control). Total rat RNA, that is known to have reduced immunogenicity, was also used as a control.

FIG. 5B shows the absolute quantification of Tumor necrosis factor (TNF)-α (cytokine) levels in supernatants of hDCs that were transfected with Cluc NotI IVT RNA using ELISA (Kariko, et al., (2011)). Cluc NotI IVT RNA (or control RNA—poly I:C) were introduced into hDCs, and supernatants were collected 24 hours after transfection. The supernatants were then probed for the secretion of TNF-α. Higher cytokine secretion is observed with Cluc NotI IVT RNA from 37° C. transcription reactions without subsequent removal of the dsRNA (IVT 37° C.) as compared to Cluc NotI IVT RNA from 55° C. transcription reactions without subsequent removal of the dsRNA (IVT 55° C.) or HPLC-purified Cluc NotI IVT RNA (IVT 37° C._HPLC) indicating low immunostimulatory properties of IVT RNA synthesized at 55° C. Resquimod (R848), an imidazoquinoline compound, used as a positive control showed increased cytokine secretion. Total rat RNA, that is known to have reduced immunogenicity, was used as a control.

DETAILED DESCRIPTION

Figure 1B:
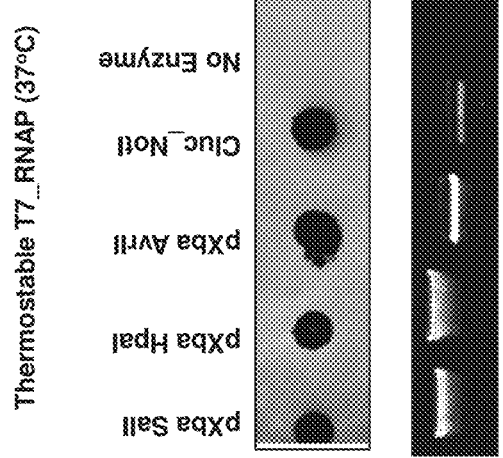
FIGS. 1A-1B shows the presence of dsRNA contaminants in IVT RNAs from different DNA templates that were synthesized under standard conditions (37° C.). The DNA templates used were pXba SalI (6 kb), pXba HpaI (9 kb), pXba AvrII (2.5 Kb), and Cluc NotI (3 kb). Crude IVT reactions were subjected to immunoblot analyses using a monoclonal antibody (mAb-J2) specific for any form of dsRNA (Schonborn, et al., (1991), Nucleic Acids Research 19(11) 2993-3000; obtained from English and Scientific Consulting, Budapest, Hungary). The intensity of the blackness on the immunoblot correlates with antibody binding to dsRNA contaminants.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications referred to herein, as well as U.S. Provisional Application Ser. No. 62/522,877 filed Jun. 21, 2017, and U.S. patent application Ser. No. 15/820,656 filed Nov. 22, 2017, are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "in vitro transcription" (IVT) refers to a cell-free reaction in which a DNA template (e.g. a double-stranded DNA template) is copied by a DNA-directed RNA polymerase to produce a product that contains RNA molecules that have been copied from the template.

As used herein, the term "DNA template" or "template DNA" refers to a double-stranded DNA molecule that is transcribed in an IVT reaction. DNA templates have a promoter (e.g., a T7, T3 or SP6 promoter) recognized by the RNA polymerase upstream of the region that is transcribed.

As used herein, the term "RNA product" refers to the product of an IVT reaction. The RNA product of IVT contains a mixture of RNA molecules and, depending on how the transcription is done, may contain dsRNA molecules. The molecular events that generate dsRNA molecules in IVT reactions is unknown. dsRNA molecules can be detected using an antibody that is specific for dsRNA or by liquid chromatography (e.g., HPLC), for example.

As used herein, the terms "less immunostimulatory" and "less immunogenic" (or "reduced immunostimulation" or "reduced immunogenicity") are used interchangeably to describe a reduction in an immune response (e.g., a reduction of interferon or cytokine expression) relative to a reference sample, e.g., a control. A decrease in immunostimulation or immunogenicity may be a response that is reduced by at least 20%, at least 40%, at least 60%, at least 80%, at least a 90%, or at least a 95% relative to the control.

As used herein, the terms "reduced dsRNA", "less dsRNA" and "fewer dsRNA molecules" are used interchangeably to refer to a sample that has an amount of dsRNA that is at least 20%, at least 40%, at least 60%, at least 80%, at least 90%, or at least 95% less than the amount of dsRNA in a reference or control sample.

As used herein, the term "thermostable RNA polymerase" refers to an RNA polymerase that has a temperature optimum of greater than 44° C., such as at a temperature optimum of at least 50° C., at least 55° C., or at least 60° C. In many embodiments a thermostable RNA polymerase may be a variant of a wild type mesophilic RNA polymerase, where the wild type mesophilic RNA polymerase is substantially inactive at the temperature at which the thermostable variant is optimally active. The thermostable RNA polymerase may be purified before use. The RNA polymerase may be stored in a storage buffer before being added to a reaction mixture or therapeutic formulation.

As used herein, the term "step that removes dsRNA" refers to any method that can be used to specifically remove dsRNA, but not RNA that is not dsRNA, from a sample. For example, dsRNA can be removed by chromatography (e.g., HPLC). In another example, dsRNA can be removed using an RNase that is specific for dsRNA, e.g., RNase III, RNase V1, Dicer, or Chipper. A step that removes dsRNA from a sample does not need to remove all of the dsRNA from the sample. Rather, such a step should remove at least 80%, at least 90% or at least 95% (up to 100%) of the dsRNA from the sample. A method that is performed "in the absence of a step that removes dsRNA" does not include any method step that specifically removes dsRNA, but not RNA that is not dsRNA, from a sample (such as but not limited to the dsRNA-removing steps discussed above).

As used herein, the term "variant" refers to a protein that comprises or consists of an amino acid sequence that is different from a reference (e.g. naturally occurring) amino acid sequence (i.e., having less than 100% sequence identity to the amino acid sequence of a reference (e.g. naturally occurring protein)) but that is at least 80%, at least 85%, at least 90%, at least 95%, at least 97%, at least 98% or at least 99% identical to the reference (e.g. naturally occurring) amino acid sequence.

As used herein, the term "introducing" refers to any means for introducing a nucleic acid into cell, including, but not limited to, transfection, microinjection, electroporation and lipid-mediated methods.

As used herein, the term "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES.

The term "non-naturally occurring" refers to a composition that does not exist in nature.

Any protein described herein may be non-naturally occurring, where the term "non-naturally occurring" refers to a protein that has an amino acid sequence and/or a post-translational modification pattern that is different from the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different from a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an epitope tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state.

In the context of a nucleic acid, the term "non-naturally occurring" refers to a nucleic acid that contains: a) a sequence of nucleotides that is different from a nucleic acid in its natural state (i.e., having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

In some embodiments, a method for introducing an IVT RNA product into mammalian cells is provided. In embodiments, the IVT RNA being tested does not contain pseudouridine. The method may be performed in vitro or in vivo. For example, the mammalian cells may be in vitro or may be ex vivo. Alternatively, the IVT RNA product may be introduced into mammalian cells by administering the IVT RNA product to a mammalian subject. In any of these embodiments, the method may comprise: (a) transcribing a template DNA with a thermostable RNA polymerase at a temperature of greater than 44° C. (e.g., a temperature of at least 45° C., at least 50° C., at least 55° C. or at least 60° C., up to about 70° C. or 75° C.) to produce an RNA product; and (b) introducing the RNA product into mammalian cells. The RNA product is generally introduced into mammalian cells at temperatures of about 37° C. Because the RNA product contains significantly reduced amounts of dsRNA as compared to an RNA product (made in the presence of U, A, G and C nucleotides) produced by transcription from the template DNA with the polymerase at a lower temperature of e.g. about 37° C., the method may be done in the absence of a step that removes any dsRNA from the RNA product (i.e., a purification step or enzyme treatment step) prior to introducing the RNA product into the cells, i.e., between steps (a) and (b) of the method. In this method, the RNA product obtained in step (a) and introduced into the cells in step (b) is believed to be less immunostimulatory than a control RNA product produced by transcribing the template DNA with the polymerase at a temperature of 37° C., when the immunostimulatory effect of the control RNA (containing nucleotides U, A, G and C but not modified nucleotides of U) is evaluated by introducing the control RNA into the cells in the absence of a step that would remove dsRNA from control RNA product. As illustrated below, the immunostimulatory effect of an RNA product can be measured by introducing the RNA product to mammalian cells and measuring the expression of markers for innate immunity (e.g., interferons and cytokines, among many others) by the cells. Immunogenicity may be measured by ELISAs (e.g. as described previously (Kariko, et al., (2011); Weissman, et al., (2012)). For example, mammalian cells are transfected with the IVT RNA product, the cells are harvested, and the cell supernatant is assayed for levels of IFN-α and/or TNF-α.

Because the results shown below indicate that this effect appears to be based on the temperature of the IVT reaction rather than the polymerase used, the method may be done using any suitable thermostable variants of a bacteriophage RNA polymerase. In some embodiments, the polymerase may be a thermostable variant of the T7, T3 and SP6 RNA polymerases, which have been well characterized. Guidance for making thermostable variants of those RNA polymerases can be found in PCT/US2017/013179 and U.S. application Ser. No. 15/594,090. In some embodiments, the thermostable RNA polymerase used in the method may be a variant of the wild type T7 RNA polymerase of SEQ ID NO:1. In particular embodiments, the thermostable RNA polymerase may have an amino acid sequence that is at least 80% or at least 90% identical to SEQ ID NO:1 (but less than 100% identical to SEQ ID NO:1) and may comprise an amino acid substitution at one or more positions corresponding to positions selected from 109, 205, 388, 534, 567 and 618 of SEQ ID NO:1, as described in PCT/US2017/013179. For example, the variant may include a mutation at a position corresponding to 567 in SEQ ID NO:1 for example V567P.

The amino acid sequence of the full length T7 RNA polymerase is shown below (SEQ ID NO: 1)
MNTINIAKNDFSDIELAAIPFNTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISPMFQPCVVPPKPWTGITGGGYWANGRRPLALVRTH

SKKALMRYEDVYMPEVYKAINIAQNTAWKINKKVLAVANVITKWKHCPVE

-continued

```
DIPAIEREELPMKPEDIDMNPEALTAWKRAAAAVYRKDKARKSRRISLEF

MLEQANKFANHKAIWFPYNMDWRGRVYAVSMFNPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLAYGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVHSQDGSHLRKTVVWAHE

KYGIESFALIHDSFGTIPADAANLFKAVRETMVDTYESCDVLADFYDQFA

DQLHESQLDKMPALPAKGNLNLRDILESDFAFA
```

In some embodiments, the RNA product may encode a protein, e.g., a therapeutic protein or a protein expected to alter the cells into which it is introduced and, as such, the RNA molecules in the RNA product may have a 5' untranslated region (5' UTR), one or more coding sequences, and a 3' translated region (3' UTR), where the 3' and 5' UTRs facilitate translation of the one or more coding sequence to produce a protein within the cells. In other embodiments, the RNA product may be a therapeutic RNA. In some embodiments the RNA product may be a guide RNA, a short hairpin RNA, a siRNA, a microRNA, a long noncoding RNA, or a protein-coding RNA (which may encode a recombinant protein or a protein that is native to the cells). In some embodiments, the RNA product may contain modified nucleotides (triphosphates for which can be added to the IVT reaction). In these embodiments, modified nucleotides may be incorporated into the IVT RNA. Incorporation of modified nucleotides can increase in translation efficiency of the RNA and increased stability of the RNA. Modifications can be present either in the sugars (e.g., 2'-fluororibose, ribose, 2'-deoxyribose, arabinose, and hexose); and/or in the phosphate groups (e.g., phosphorothioates and 5'-N-phosphoramidite linkages); and/or in the nucleotide base (for example, see: U.S. Pat. No. 8,383,340; WO 2013/151666; U.S. Pat. No. 9,428,535 B2; US 2016/0032316). In some embodiments, the RNA product may be altered during or after the transcription reaction, e.g., to decrease the rate at which the RNA products are degraded in the cells. In some embodiment, the RNA product may contain capped RNAs (see, for example: WO 2016/090262; WO 2014/152673; WO 2009/149253; WO 2009/149253; Strenkowska, et al., (2016), Nucleic Acids Research, 44(20):9578-90). RNAs with poly A tails of varying length and labeled RNAs can also be produced.

In some embodiments, the method may further comprise testing the RNA product for an immune-stimulatory effect, without performing a step that removes the dsRNA from the RNA product. As noted above, this may be done in a variety of different ways. The method may comprise measuring the immunogenicity of the RNA product obtained in step (a) before or after step (b). In some embodiments, the method comprises the steps of comparing the immunogenicity of the RNA product with the immunogenicity of a control RNA product. For example, the method may comprise the steps of: (i) producing a control RNA product by transcribing the template DNA with the thermostable RNA polymerase at a temperature of 37° C. and, in the absence of a step that removes any dsRNA from the control RNA product, measuring the measuring the immunogenicity of the control RNA product; and (ii) comparing the immunogenicity measured for the RNA product with the immunogenicity measured for the control RNA product. For example, in some embodiments, the amount of dsRNA in the RNA product may be measured using a dsRNA-specific antibody or by liquid chromatography, for example.

In any embodiment, the in vitro transcription may be done using natural NTPs, i.e., GTP, CTP, UTP and ATP to produce a product that does not contain not contain modified nucleosides.

In any embodiment, the in vitro transcription may be done using NTPs corresponding to G, C, U and A in the absence of pseudo-uridine triphosphate to produce a product that does not contain not contain pseudo-uridine. The cells into which the RNA product is introduced may be in vitro (i.e., cells that have been cultured in vitro on a synthetic medium). In these embodiments, the RNA product may be transfected into the cells. In other embodiments, the cells into which the RNA product is introduced may be in vivo (cells that are part of a mammal). In these embodiments, the introducing may be done by administering the RNA product to a subject in vivo. In some embodiments, the cells into which the RNA product is introduced may present ex vivo (cells that are part of a tissue, e.g., a soft tissue that has been removed from a mammal or isolated from the blood of a mammal).

Methods for making a formulation are also provided. In some embodiments, the method may comprise combining an RNA product made by transcribing a template DNA with a thermostable RNA polymerase at a temperature of greater than 44° C. with a pharmaceutically acceptable excipient to produce a formulation. In some embodiments, the RNA product may be combined with the pharmaceutically acceptable excipient in the absence of a step that removes any dsRNA from the RNA product. In some embodiments, the method comprises (a) transcribing a template DNA with a thermostable RNA polymerase at a temperature of greater than 44° C. to produce an RNA product; and (b) combining the RNA product with a pharmaceutically acceptable excipient; wherein the method is done in the absence of a step that removes any dsRNA from the RNA product between steps (a) and (b).

In some embodiments, the RNA can be formulated in a suitable excipient and effective therapeutic dose for introducing into a host for achieving a desired therapeutic effect. The formulation should lack adverse immune-stimulatory effects caused by dsRNA.

The product RNA is not packaged into a virus particle prior to administration.

In some embodiments, this method may further comprise administering the formulation to a subject, where the subject may be a human or any non-human animal (e.g., mouse, rat, rabbit, dog, cat, cattle, swine, sheep, horse or primate). Depending on the subject, the RNA (modified or unmodified) can be introduced into the cell directly by injecting the RNA or indirectly via the surrounding medium. Administration can be performed by standardized methods. The RNA can either be naked or formulated in a suitable form for administration to a subject, e.g., a human. Formulations can include liquid formulations (solutions, suspensions, dispersions), topical formulations (gels, ointments, drops, creams), liposomal formulations (such as those described in: U.S. Pat. No. 9,629,804 B2; US 2012/0251618 A1; WO 2014/152211; US 2016/0038432 A1).

In some embodiments, the in vitro synthesized RNA product can be delivered into the cells by packaging them into nanoparticles such as cationic lipids and polymers, non-viral carriers like protamine. Direct introduction of the RNA into the cell using microinjection, electroporation, sonoporation can also be implemented. The delivery (localized or systemic) and the packaging of the RNA (with or without modifications) can be performed at temperatures optimal for the delivery approach or the formulation used (such as those described in: U.S. Pat. No. 9,629,804 B2; US 2012/0251618 A1; WO 2014/152211; US 2016/0038432 A1; US 2016/0032316 A1; U.S. Pat. No. 9,597,413 B2; US 2012/0258176).

A therapeutic formulation is also provided. In some embodiments, the formulation may comprise: (a) an RNA product produced by transcribing a template DNA using a thermostable RNA polymerase at a temperature of greater than 44° C.; and (b) pharmaceutically acceptable excipient. Consistent with the above, the formulation may be made in the absence of a step that removes dsRNA from the RNA product.

Also provided is an RNA product produced by transcribing a template DNA using a thermostable RNA polymerase at a temperature of greater than 44° C., for use as a medicament. Also provided is a therapeutic formulation of the invention, for use as a medicament.

Also provided is a method comprising: (a) transcribing a template DNA with a thermostable RNA polymerase at a temperature of greater than 44° C. to produce an RNA product; and (b) measuring an immunostimulatory effect of the RNA product in the absence of a step that removes dsRNA from the RNA product. As discussed above, the immunostimulatory effect of an RNA product can be measured by introducing the RNA product to mammalian cells and measuring the expression of markers for innate immunity (e.g., interferons and cytokines, among many others) by the cells. These cells may be in vitro, in vivo or ex vivo.

In some embodiments, the methods and compositions described herein may be used to make polyribonucleotides which when transfected into eukaryotic cells or prokaryotic cells in vivo or in vitro can change the cell phenotype by production of proteins or by affecting expression of targets in the cell. This is best achieved if one can avoid generating an immunostimulatory response (triggered by dsRNA) that would undermine the viability of the target cells.

RNA products of IVT can be used for encoding proteins such as antigens for vaccines, for cancer immunotherapies (such as those described in: U.S. Pat. No. 8,217,016 B2; US 2012/0009221 A1; US 2013/0202645A1; U.S. Pat. No. 9,587,003 B2; Sahin, et al., (2014); allergy tolerance (such as those described in Sahin, et al., (2014), for producing recombinant or naturally occurring protein for protein replacement therapeutics (such as those described in: US 2016/0032316 A1; US 2016/0032316; U.S. Pat. No. 8,680,069; WO 2013/151736; WO 2014/152940; U.S. Pat. Nos. 9,181,321; 9,220,792 B2; 9,233,141 B2; Sahin, et al., (2014)), supplementation therapeutics (such as those described in Sahin, et al., (2014)), cell reprogramming (such as those described in: US 2011/0143436 A1; U.S. Pat. Nos. 8,802,438; 9,371,544; WO/2009077134 A2; Sahin, et al., (2014)), genome editing/engineering (such as those described in Sahin, et al., (2014)).

EMBODIMENTS

Embodiment 1. A method, comprising: (a) transcribing a template DNA with a thermostable RNA polymerase at a temperature of greater than 44° C. to produce an RNA product; and (b) introducing the RNA product into mammalian cells, wherein the method is done in the absence of a step that removes any dsRNA from the RNA product between steps (a) and (b).

Embodiment 2. The method of embodiment 1, wherein the RNA product administered in (b) is less immunostimulatory than a control RNA product produced by transcribing the template DNA with the polymerase at a temperature of 37° C., wherein the control RNA is introduced into the cells in the absence of a step that removes any dsRNA from the control RNA product.

Embodiment 3. The method of any prior embodiment, wherein the transcribing is done at a temperature of at least 50° C.

Embodiment 4. The method of any prior embodiment, wherein the thermostable RNA polymerase is a variant of a bacteriophage RNA polymerase.

Embodiment 5. The method of any prior embodiment, wherein the thermostable RNA polymerase is a variant of the wild type T7 RNA polymerase of SEQ ID NO:1.

Embodiment 6. The method of any prior embodiment, including one or more of the following: (i) the RNA product encodes a therapeutic protein, (ii) the RNA product does not include pseudouridine and/or (iii) the RNA product is preferably not delivered in a virus particle.

Embodiment 7. The method of any prior embodiment, wherein the RNA product is a therapeutic RNA.

Embodiment 8. The method of any prior embodiment, wherein the RNA product is selected from a guide RNA, a short hairpin RNA, a siRNA, a microRNA, a long noncoding RNA, a mRNA encoding a recombinant protein or a native protein, an RNA containing modified nucleotides, and a capped mRNA.

Embodiment 9. The method of any prior embodiment, further comprising assaying the RNA product of step (a) for the presence of dsRNA, without performing a step that removes any dsRNA from the RNA product.

Embodiment 10. The method of any prior embodiment, wherein the cells are cells cultured in vitro.

Embodiment 11. The method of any of embodiments 1-9, wherein the introducing is done by administering the RNA product to a subject in vivo.

Embodiment 12. The method of any of embodiments 1-9, wherein the cells are ex vivo.

Embodiment 13. A method, comprising: combining an RNA product made by transcribing a template DNA with a thermostable RNA polymerase at a temperature of greater than 44° C. with a pharmaceutically acceptable excipient to produce a formulation.

Embodiment 14. The method of embodiment 13, further comprising administering the formulation to a subject.

Embodiment 15. The method of any of embodiments 13 and 14, wherein the RNA product is combined with the pharmaceutically acceptable excipient in the absence of a step that removes any dsRNA from the RNA product.

Embodiment 16. A therapeutic formulation comprising: (a) an RNA product produced by transcribing a template DNA using a thermostable RNA polymerase at a temperature of greater than 44° C.; and (b) pharmaceutically acceptable excipient.

Embodiment 17. A method, comprising: (a) transcribing a template DNA with a thermostable RNA polymerase at a temperature of greater than 44° C. to produce an RNA product; (b) measuring the immunogenicity of the RNA product in the absence of a step that removes any dsRNA from the RNA product.

EXAMPLES

Aspects of the present teachings can be further understood in light of the following examples, which should not be construed as limiting the scope of the present teachings in any way.

Synthesis of IVT mRNA—IVT reactions were performed in 41 mM Tris-HCl pH 8.0, 50 mM NaCl, 19 mM $MgCl_2$, 5.5 mM DTT, 1 mM spermidine, 4 mM of each ribonucleotide, 4.15 units/5 mL yeast inorganic pyrophosphatase, 1000 units/mL murine ribonuclease inhibitor, 30 nM DNA template and 30 nM T7 RNA polymerase. The DNA template was plasmid DNA that was linearized using restriction endonucleases at specific sites downstream of the T7 promoter. Reactions were performed at various temperatures ranging from 37° C. to 55° C. For the synthesis of modified mRNA, UTP was replaced with triphosphate derivatives of pseudouridine (Trilink Biotechnologies, San Diego, Calif.) in the IVT reaction. A 125-nt poly(A) tail was template-encoded in mRNAs that were used for transfection experiments. IVT mRNAs were processed through a spin column (MEGAClear™, Thermo Fisher Scientific, Waltham, Mass.) to remove unincorporated nucleotides before performing capping reactions or HPLC purification. Capped mRNAs were generated for the transfection experiments using vaccinia capping enzyme (New England Biolabs, Ipswich, Mass.), and 2' O-methyltransferase (New England Biolabs, Ipswich, Mass.) was added to the reaction to attain the Cap1 structure required for efficient translation.

dsRNA immunoblot—IVT RNAs were blotted onto Nytran™ SuPerCharge (SPC) Blotting Membranes (GE Healthcare, Marlborough, Mass.). The dried membranes were blocked for at least 1 hour in blocking buffer (TBS Blotto, Santa Cruz Biotechnologies, Dallas, Tex.) and then incubated with mAb-J2 (1:500 dilution; English and Scientific Consulting, Budapest, Hungary) for at least 4 hours. IRDye-800-conjugated donkey anti-mouse secondary antibody (1:5000; LiCor, Lincoln, Nebr.) was used for detection using an Odyssey imaging system (LiCor, Lincoln, Nebr.).

HPLC purification of IVT RNA—HPLC purification of IVT RNA was performed as described previously (Kariko, et al., (2011); Weissman, et al., (2012)). RNA from IVT reactions was loaded onto an analytical column with a matrix composed of alkylated non-porous polystyrene-divinylbenzene copolymer microspheres that was obtained from Transgenomic, Omaha, Nebr. The column was equilibrated with 38% buffer B (0.1 M triethylammonium acetate pH 7.0, 25% acetonitrile) and loaded with the IVT RNA (10 µg per run) followed by a linear gradient of buffer B (38% to 65%). Fractions were collected for the major IVT RNA peak (II), and the fractions were desalted and concentrated using Amicon® Ultra-15 centrifugation units (EMD Millipore, Billerica, Mass.). RNA was diluted with nuclease-free water and subjected to capping.

Cell culture and transfection—hDCs were cultured in lymphocyte growth medium with 50 ng/mL GM-CSF and 50 ng/mL IL-4 (Lonza, Portsmouth, N.H.) for four days prior to transfection. HEK293 cells were cultured in Dulbecco's modified Eagle's medium (DMEM) supplemented with 2 mM L-glutamine and 10% fetal calf serum (Thermo Fisher Scientific, Waltham, Mass.). Capped poly-adenylated IVT mRNA (500 ng) was complexed with either Lipofectamine (Thermo Fisher Scientific, Waltham, Mass.) or TransIT®. Transfection was performed as recommended by the manufacturer.

Translation efficiency—The translation efficiency was measured as relative luciferase activity from the transfected IVT Cluc NotI mRNA, as measured from the supernatant of transfected cells using the BioLux® Cypridina Luciferase Assay Kit (New England Biolabs, Ipswich, Mass.). Luminescence was measured using the Centro LB 960 Microplate Luminometer from Berthold Technologies (Wildbad, Germany). For each reaction, 20 µL of the supernatant was assayed 12 hours after transfection. The results in triplicate showed that the translation efficiency for the IVT RNA synthesized by thermostable T7 RNA polymerase at 55° C. was similar to the translation efficiency of IVT RNA synthesized by wild type T7 RNA polymerase at 37° C. and by IVT RNA synthesized by wild type T7 RNA polymerase at 37° C. after an HPLC column treatment at this incubation time (where each sample provided 300,000-400,000 relative luciferase units). The negative controls (TransIT), PBS, Polyinosinic-polycytidylic acid (PolyI:C) synthetic dsRNA (Invivogen, San Diego, Calif.), and Resiquimod (R848) small molecule immune activator (Invivogen, San Diego, Calif.)) all were consistently negative with zero detectable relative luciferase units.

Immunogenicity assays—Immunogenicity was measured by ELISAs as described previously (Kariko et al., (2011); Weissman, et al., (2012)). Supernatant from cells that were transfected with IVT mRNA was harvested 24 hours after transfection and assayed for levels of IFN-α (PBL Interferon Source, Piscataway, N.J.) (for TransIT-complexed RNA) and TNF-α (Thermo Fisher Scientific, Waltham, Mass.) (for Lipofectamine-complexed RNA). A standard curve using purified IFN-α or TNF-α was used to quantify the cytokines.

Figure 1A:
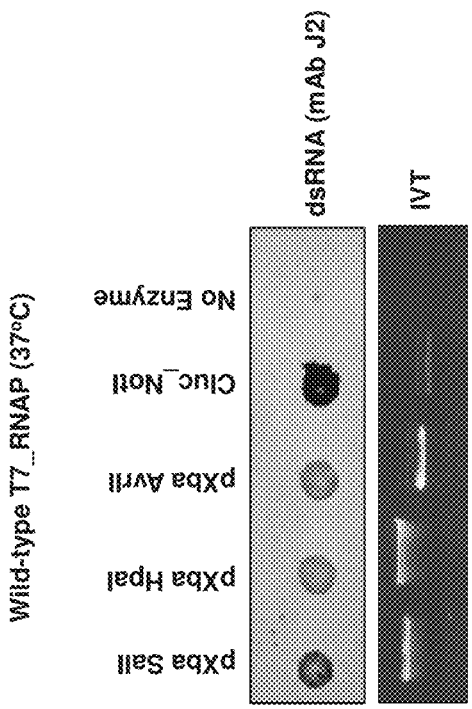
Figure 2A:
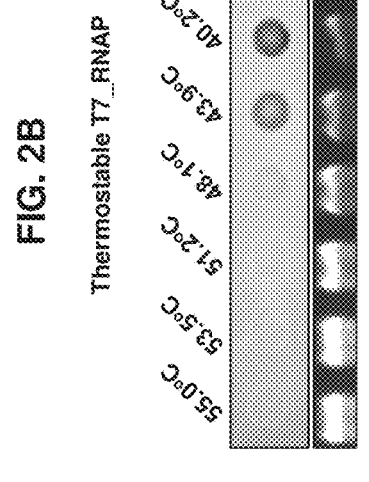
FIGS. 2A-2D shows the reduction in amounts of dsRNA in IVT reactions that were performed at higher temperatures either because the wild-type T7 polymerase was inactive or because the thermostable T7 polymerase did not produce dsRNA. Activity was determined by the amount of IVT RNA observed on the 1.2% agarose gel. The observed effect was independent of the length of the DNA template.
Figure 2B:
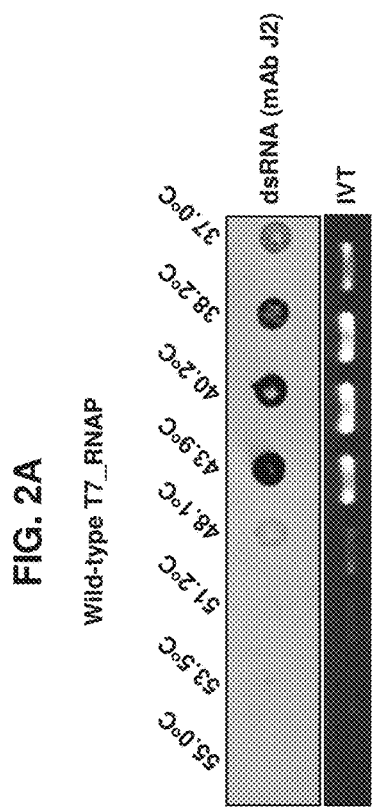
Figure 2C:
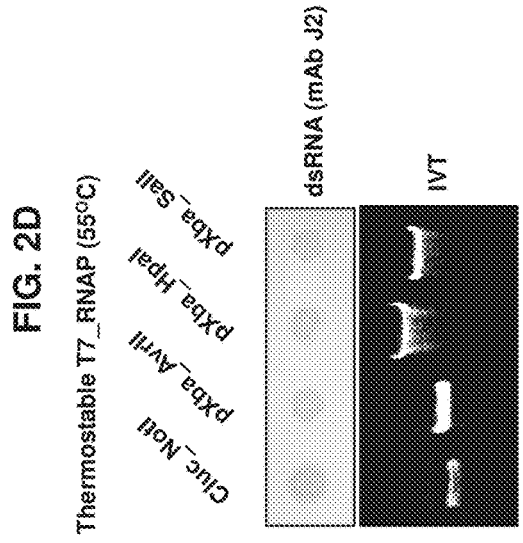
Figure 2D:
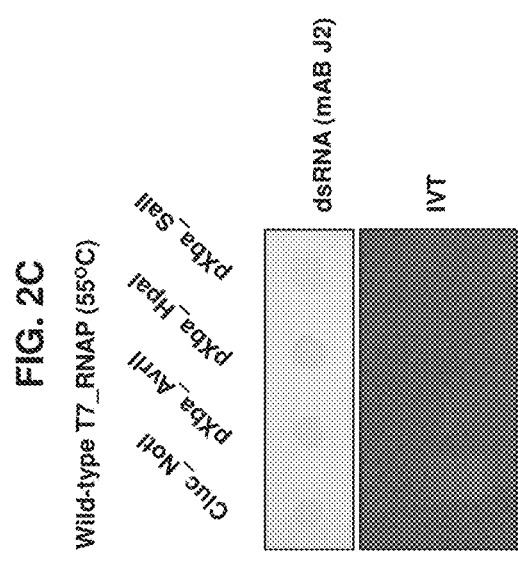
Figure 3:
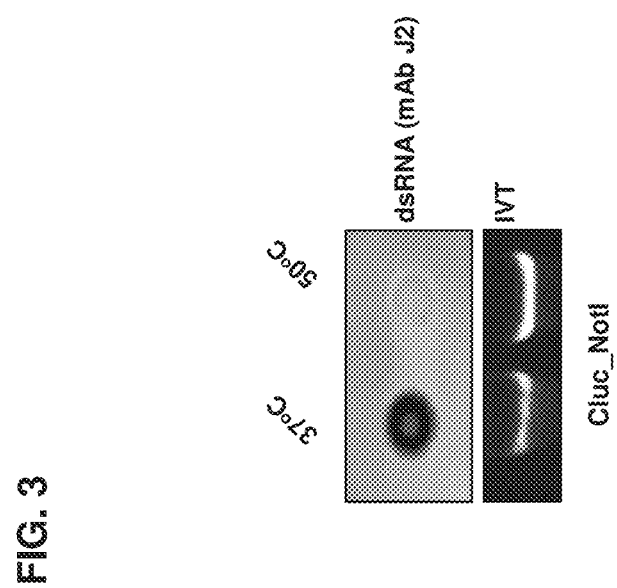
FIG. 3 shows the effect of high temperature on dsRNA formation in IVT reactions using a commercially available thermostable T7 RNA polymerase from Toyobo Life Science Department, Osaka, Japan on Cluc NotI template DNA. IVT was performed at 37° C. or 50° C. Only the amount of dsRNA contaminants was reduced at 50° C. while significant amounts of Cluc NotI RNA were detected on a 1.2% agarose gel. This data demonstrates that the temperature of the reaction rather than the particular thermostable T7 RNA polymerase is responsible for reduction of dsRNA.
Figure 4:
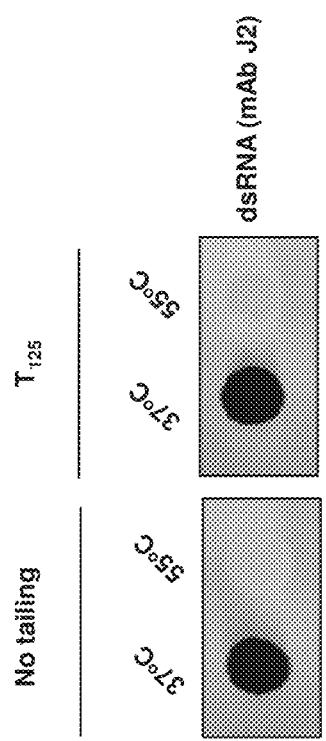
FIG. 4 shows the temperature dependent reduction of dsRNA associated with IVT of Cluc NotI RNA that either lacks a poly A tail (no tailing) or was polyadenylated with a tail-length of 125 nucleotides (T125). Both RNAs contained a modified nucleotide-pseudouridine instead of uridine.
Figure 5A:
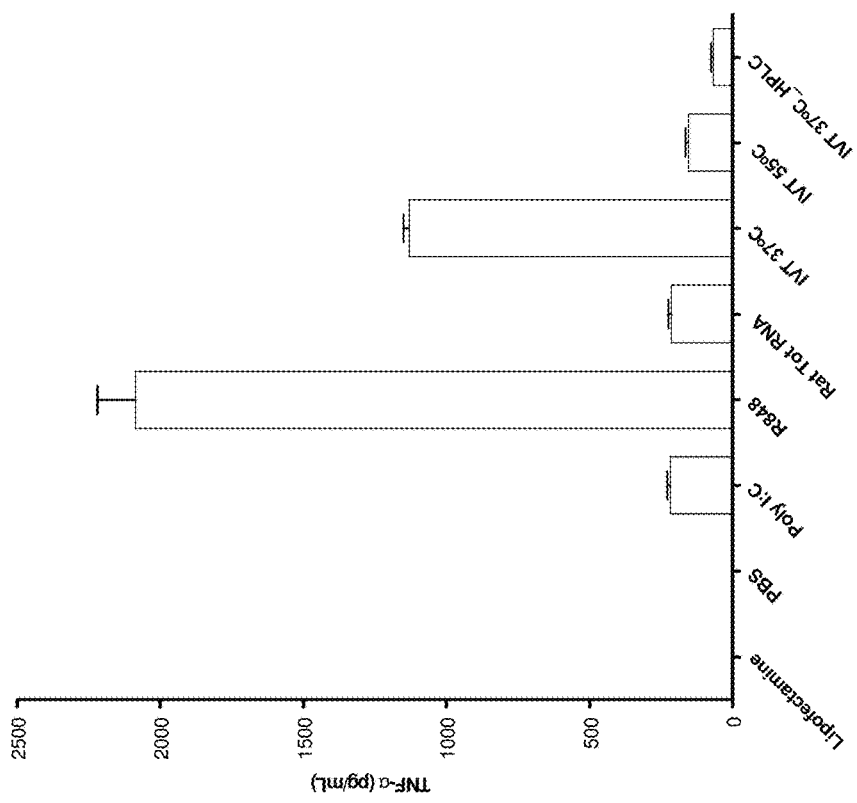
FIGS. 5A-5B shows activation of interferons and cytokines (represented by IFN-α and TNF-α respectively) indicative of an immune response activation in human dendritic cells (hDCs) that were transfected with Cluc NotI IVT RNA from reactions that were performed with wild-type T7 RNA polymerase at 37° C. or with a thermostable variant of T7 RNA polymerase at 55° C. Poly I:C, a synthetic analog of dsRNA and Resiquimod (R848), an activator of Toll-like receptors are used as controls for interferon activation. Negative controls included TransIT® (Mirus Bio, Madison, Wis.) transfection reagent alone and PBS.
Figure 5B:
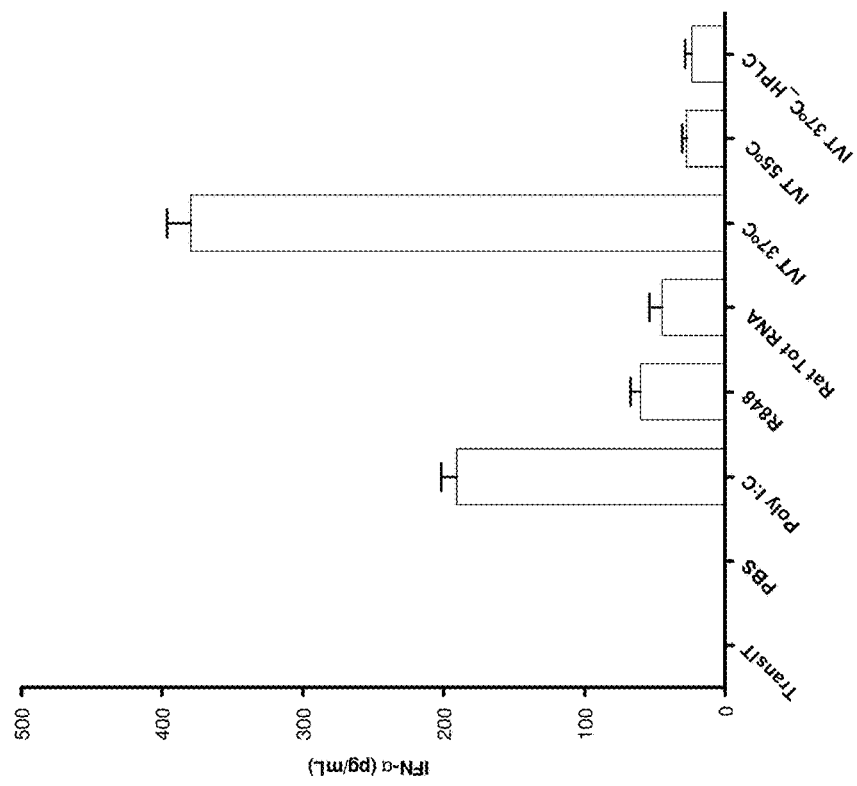

Results of experiments performed using the protocols described above are shown in FIGS. 1A-1B, 2A-2B, 3, 4 and 5A-5B. These results show that IVT at a temperature greater than 44° C. (e.g., at a temperature of greater than 44° C.) results in a product that has less dsRNA and is less immunogenic than a product transcribed at a lower temperature (e.g., a temperature of 37° C. or below).

---

What is claimed is:

1. A method for producing an RNA product with reduced immunogenicity, comprising:
   (a) combining a DNA and a thermostable RNA polymerase at a temperature of greater than 44° C., the RNA polymerase variant having an amino acid sequence that has at least 90% sequence identity with SEQ ID NO:1 and having an amino acid substitution at a position corresponding to position 567 and optionally at a position corresponding to position 388; and
   (b) producing the RNA product comprising a single strand RNA having reduced immunogenicity compared with an RNA product produced by an RNA polymerase at 37° C.

2. A method according to claim 1, further comprising combining the single stranded RNA with a pharmaceutically acceptable excipient.

3. A method according to claim 2, further comprising introducing the formulation into a mammalian cell.

4. The method of claim 2, further comprising administering the formulation to a subject.

5. The method of claim 1, wherein the transcribing is done at a temperature of at least 50° C.

6. The method of claim 1, wherein the thermostable RNA polymerase has a further amino acid substitution at a position selected from positions 109, 205, 534, and 619.

7. The method of claim 1, wherein the thermostable RNA polymerase has an amino acid substitution at a position corresponding to position 567, wherein the substation is V567P.

8. The method of claim 1, wherein the RNA product encodes a therapeutic protein.

9. The method of claim 1, wherein the RNA product is a therapeutic RNA.

10. The method of claim 1, wherein the RNA product is selected from a guide RNA, a short hairpin RNA, a siRNA, a microRNA, a long noncoding RNA, a mRNA encoding a recombinant protein or a native protein, an RNA containing modified nucleotides, and a capped mRNA.

11. The method of claim 1 further comprises producing the RNA product comprising a single strand RNA having reduced immunogenicity in the absence of a step that removes any double-stranded RNA (dsRNA) from the RNA product.

* * * * *